US009418390B2

(12) United States Patent
Chun et al.

(10) Patent No.: US 9,418,390 B2
(45) Date of Patent: Aug. 16, 2016

(54) DETERMINING AND COMMUNICATING USER'S EMOTIONAL STATE RELATED TO USER'S PHYSIOLOGICAL AND NON-PHYSIOLOGICAL DATA

(71) Applicant: Intel Corporation, Santa Clara, CA (US)

(72) Inventors: Anthony L. Chun, Los Altos, CA (US); Glen J. Anderson, Beaverton, OR (US); Albert Yosher, Haifa (IL)

(73) Assignee: INTEL CORPORATION, Santa Clara, CA (US)

( * ) Notice: Subject to any disclaimer, the term of this patent is extended or adjusted under 35 U.S.C. 154(b) by 885 days.

(21) Appl. No.: 13/625,588

(22) Filed: Sep. 24, 2012

(65) Prior Publication Data
US 2014/0089399 A1 Mar. 27, 2014

(51) Int. Cl.
*G06F 15/16* (2006.01)
*G06Q 50/00* (2012.01)
*A61B 5/16* (2006.01)
*H04L 12/58* (2006.01)

(52) U.S. Cl.
CPC *G06Q 50/01* (2013.01); *A61B 5/16* (2013.01); *A61B 5/165* (2013.01); *H04L 51/10* (2013.01)

(58) Field of Classification Search
CPC .......... A61B 5/16; A61B 5/165; H04L 51/10; G06Q 50/01
USPC ........................... 709/201–206; 600/300–301
See application file for complete search history.

(56) References Cited

U.S. PATENT DOCUMENTS

| 7,403,972 B1 * | 7/2008 | Lau | G06Q 50/22 709/206 |
| 7,543,330 B2 * | 6/2009 | Garbow | H04L 63/0263 600/300 |
| 7,874,983 B2 | 1/2011 | Zancho et al. | |

(Continued)

FOREIGN PATENT DOCUMENTS

EP 1607842 12/2005

OTHER PUBLICATIONS

International Search Report and Written Opinion, mail date Oct. 11, 2013, PCT/ISA/210, PCT/ISA/220, and PCT/ISA/237, total of 11 pages.

(Continued)

*Primary Examiner* — Bharat N Barot
(74) *Attorney, Agent, or Firm* — Pillsbury Winthrop Shaw Pittman LLP

(57) ABSTRACT

According to various aspects of the present disclosure, a system and associated method and functions to determine an emotional state of a user are disclosed. In some embodiments, the disclosed system includes a data acquisition unit, an emotion determination unit, and an emotion reporting unit. The data acquisition unit is configured to detect user information including physiological and non-physiological data associated with the user. The emotion determination unit is operatively connected to the data acquisition unit, and is configured to process the user information to determine an emotional state of the user. The emotion reporting unit is configured to communicate the emotional state based on a predetermined reporting preference to an application of a communication device, e.g., a social-networking application to share the emotional state of the user such that other members of the social network associated with the user are notified of the user's emotional state.

30 Claims, 2 Drawing Sheets

(56) References Cited

U.S. PATENT DOCUMENTS

| | | | |
|---|---|---|---|
| 7,944,448 B2* | 5/2011 | Iwamura | G06Q 90/00 345/473 |
| 2003/0139654 A1 | 7/2003 | Kim et al. | |
| 2005/0163302 A1* | 7/2005 | Mock et al. | 379/211.02 |
| 2011/0124977 A1 | 5/2011 | Winarski | |
| 2011/0234488 A1* | 9/2011 | Ge et al. | 345/156 |
| 2011/0301433 A1* | 12/2011 | Sadowsky | G06Q 30/0271 600/300 |
| 2012/0124122 A1 | 5/2012 | El Kaliouby et al. | |
| 2012/0135804 A1* | 5/2012 | Bender | A61B 5/165 463/36 |
| 2012/0323087 A1* | 12/2012 | Leon Villeda | A61B 5/165 600/301 |
| 2014/0052792 A1* | 2/2014 | Dunko | H04M 1/72547 709/206 |
| 2014/0059066 A1* | 2/2014 | Koloskov | G06F 17/30017 707/758 |
| 2014/0236953 A1* | 8/2014 | Rapaport | G06Q 10/10 707/740 |
| 2014/0250200 A1* | 9/2014 | Geurts et al. | 709/206 |
| 2014/0323817 A1* | 10/2014 | el Kaliouby | A61B 5/165 600/300 |

OTHER PUBLICATIONS

International Preliminary Report on Patentability mailed Apr. 2, 2015 for corresponding International Patent Application No. PCT/US2013/047945 (8 pages).

* cited by examiner

DETERMINING AND COMMUNICATING USER'S EMOTIONAL STATE RELATED TO USER'S PHYSIOLOGICAL AND NON-PHYSIOLOGICAL DATA

FIELD OF THE INVENTION

The present invention relates generally to techniques and systems to determine and communicate an emotional state of a user or an organization, and more particularly, to techniques and systems to determine and communicate an emotional state based on physiological and non-physiological information of the user.

BACKGROUND

Typically, an emotional state of a person is determined based only on his/her physiological or biological characteristics. Further, a person typically expresses his/her emotional state by manually communicating it through social networking applications (e.g., Facebook, Twitter, etc.) or other applications. However, such emotion computing and communicating techniques do not utilize user's characteristics or conditions other than his/her physiological parameters to determine the person's emotional state, and fail to automatically communicate the emotional state, e.g., in accordance with some predefined preferences.

DETAILED DESCRIPTION

Figure 1:
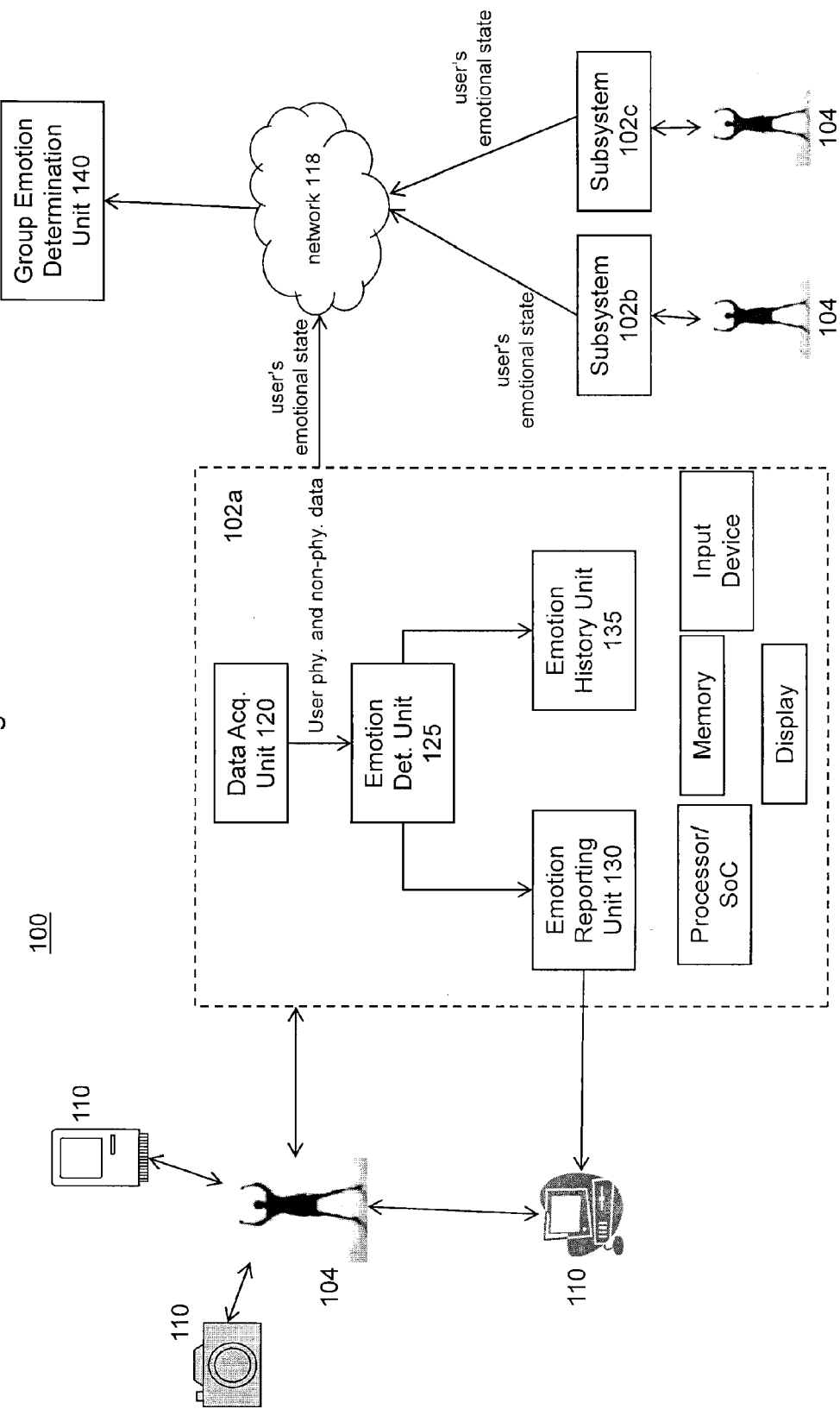
FIG. 1 is a block diagram of a system to determine an emotional state of a user and a group of users, in accordance with various embodiments of the present disclosure.

In the description that follows, like components have been given the same reference numerals, regardless of whether they are shown in different aspects. To illustrate one or more aspect(s) of the present disclosure in a clear and concise manner, the drawings may not necessarily be to scale and certain features may be shown in somewhat schematic form. Features that are described and/or illustrated with respect to one aspect may be used in the same way or in a similar way in one or more other aspects and/or in combination with or instead of the features of the other aspects of the technology disclosed herein.

In broad overview, the system and method for determining an emotional state of a user in accordance with various embodiments of the present disclosure may be implemented in connection with (or as part of) a computing and/or communication device associated with or operated by the user. By way of illustration, such computing device may be a mobile phone, a tablet computer, a personal computer, a server, a laptop, a smartphone, a gaming device, a networking device, or a wearable computing device in the form of a wrist watch, a bracelet, a pair of headphones, a pair of eyeglasses and/or other wearable computing devices. In some embodiments, the disclosed system or method is completely or partially implemented by one or more processing units implanted within the user. Along these lines, the disclosed embodiments may be implemented in association with, or as part of, one or more computing and communication devices of various form factors.

In accordance with various aspects of the present disclosure, a system for determining an emotional state of a user is presented. The system may include a data acquisition unit, an emotion determination unit, and an emotion reporting unit. The data acquisition unit may be configured to detect user information including physiological and non-physiological data associated with the user. The non-physiological data may include location of the user, ambient environment conditions, e.g., temperature, internet browsing history of the user, and/or other information not related with the body or biological features of the user. The data acquisition unit may include at least one of a camera, a microphone, an accelerometer, a gyroscope, a location sensor, a temperature sensor to detect ambient temperature, a gesture recognition sensor, and a sensor to detect a physiological parameter of the user.

In some embodiments, the emotion determination unit is operatively connected to the data acquisition unit, and is configured to process the user information to determine an emotional state of the user, e.g., based on a pattern recognition or machine learning algorithm. The emotion determination unit may process the user information based on a predetermined computation preference, such as, but not limited to, a specific user location or a specific time period.

The emotion reporting unit may be configured to communicate the emotional state based on a predetermined reporting preference to an application of a communication device to share the emotional state of the user such that an entity is notified of the user's emotional state. For example, the application may be a social-networking application (e.g., Facebook, Twitter, LinkedIn, Google+, etc.) operational on a client device (e.g., a smartphone, a tablet computer, a desktop computer) accessed by the user and connected (via the Internet) to one or more servers hosting the social network which the user is authorized to access as a member thereof. Accordingly, as part of communicating the emotional state of the user, the emotion reporting unit may be configured to activate the application (e.g., a social networking application) on the device, provide user identification information to be authenticated by the application for logging into the application, and provide a message including an indication of the determined emotional state of the user to be shared with other members (e.g., "friends," "followers," "connections," etc.) of the application on a platform provided by the application (e.g., as a "what's on your mind?" message update on Facebook, a "tweet" on Twitter, etc.). In some embodiments, the predetermined reporting preference is preselected by the user, and stored in a memory accessible by the emotion reporting unit. The predetermined reporting preference may include a specific user location or a specific time period, based on which the emotion reporting unit may determine where or when the emotional state is communicated to the application. The emotion reporting unit may be further configured to request a confirmation from the user to communicate or share the emotional state, and receive the confirmation before communicating or sharing the emotional state.

The system may also include an emotion history unit which is configured to track and store emotional states of the user determined by the emotion determination unit, e.g., based on one or more tracking criteria (e.g., user's past locations, for a past time period, etc.). The emotion history unit may then process the emotional states to determine an effect on the user caused due to the emotional states relative to the tracking criterion.

In some embodiments, the user is a member of an organization including a plurality of users other than the user. As such, the system may further include a group emotion determination unit configured to receive the emotional state of the user and an emotional state of another of the plurality of the users, and process the emotional states to determine a collective emotional state of the organization. Such collective processing of the emotional states may include removing or deleting information identifying the users from the received data which includes the emotional state of the respective users.

In accordance with various embodiments of the present disclosure, a method to determine an emotional state of a user is disclosed. The method may include detecting user information including physiological and non-physiological data associated with the user, processing the user information to determine an emotional state of the user, and communicating the emotional state based on a predetermined reporting preference to an application of a communication device associated with the user, wherein the application is configured to share the emotional state of the user such that an entity is notified of the user's emotional state. For example, the application may be a social-networking application (e.g., Facebook, Twitter, LinkedIn, Google+, etc.) operational on a client device (e.g., a smartphone, a tablet computer, a desktop computer) accessed by the user and connected (via the Internet) to one or more servers hosting the social network which the user is authorized to access as a member thereof.

The non-physiological data may include location of the user, ambient environment conditions, e.g., temperature, internet browsing history of the user, a status of user's stock portfolio, performance of user's preferred sports team or candidate in an election, and/or other information not related with the body or biological features of the user. In some embodiments, the operation of detecting user information is performed using at least one of a camera, a microphone, an accelerometer, a gyroscope, a location sensor, a temperature sensor to detect ambient temperature, a gesture recognition sensor, and a sensor to detect a physiological parameter of the user.

The predetermined reporting preference may include a specific user location or a specific time period, based on which it is determined where or when the user's emotional state is communicated to the application. The method may further include requesting a confirmation from the user to communicate the emotional state, and receiving the confirmation before communicating the emotional state.

The method may further include tracking emotional states of the user based on a predetermined tracking criterion (e.g., user's past locations, for a past time period, etc.), and processing the emotional states to determine an effect on the user caused due to the emotional states relative to the tracking criterion.

Further, the user may be a member of an organization including a plurality of users other than the user, and the method may also include receiving the emotional state of the user and an emotional state of another of the plurality of the users, and processing the emotional states to determine a collective emotional state of the organization.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Turning now to the various aspects of the disclosure, FIG. 1 depicts a non-limiting example of a system, i.e., a system 100, in which techniques for determining and communicating emotional states of users described herein are implemented. As shown, system 100 may include an emotional state determination and communication (ESDC) subsystems 102 (i.e., subsystems 102a, 102b, 102c) associated with users 104 (i.e., users 104a, 104b, 104c), and a group emotion determination unit 106 which may be operatively connected with subsystems 102 via one or more networks 108. Alternatively, one or more subsystems 102 may be connected with group emotion determination unit 106 directly. In some embodiments, users 104 are members of a same organization, e.g., a company, an educational institution, a social network, a city, a state, a country, etc. Alternatively, users 104 may be considered as a single group by virtue of being present in a same geographical area (e.g., a shopping mall) or at a same event (e.g., a concert) at the same time. As discussed in detail below, each subsystem 102 may be configured to determine an emotional state of its associated user 104, and communicate the emotional state to one or more devices 110 associated with or operated by user 104 and also to group emotion determination unit 106 (e.g., via network(s) 108). In some embodiments, group emotion determination unit 106 is configured to process the emotional states of users 104 received from respective subsystems 102 to determine an emotional state of the organization or group of users 104. In general, the user emotional states assessed by subsystems 102 and group emotion determination unit 106 (and, in general, system 100) may include happiness, sadness, anxiety, excitement, boredom, fear, indifference, calmness, anger, aggressiveness, disgust, surprise, anticipation, and/or other known emotions or emotional states.

Referring now to an example of a detail structure of ESDC subsystem 102, in some embodiments, subsystem 102a includes a data acquisition unit 120, an emotion determination unit 125, an emotion reporting unit 130, and an emotion history unit 135. Other ESDC subsystems 102 (e.g., subsystems 102b, 102c) may include similar units or modules as of subsystem 102a, or may include more or less number of units or modules than that of subsystem 102a while providing similar emotional state-related functionalities and features described herein as subsystem 102a.

In some embodiments, data acquisition unit 120 is configured to detect, acquire and/or process user information including physiological and non-physiological data associated with user 104. In the context of this disclosure, user's physiological data include data, information or signals obtained from the user's body and that are related to biological functions and activities (including physical and chemical processes) of the user's body and its parts. For example, user's physiological data may include heart rate, skin and body temperature, blood pressure, blood oxygen level, respiratory rate, posture and motion of user's body or part thereof, user's voice, and/or other known physiological information. Accordingly, in some embodiments, data acquisition unit 120 is communicatively associated with and/or includes one or more biomedical sensors for detecting or sensing signals related to user's physiology. For example, one or more sensors to detect user's heart rate, skin and body temperature, blood pressure, blood oxygen level, and/or respiratory rate, and/or an accelerometer and a gyroscope to determine user's movement and posture may be attached on or implanted within the user's body, and may be configured to acquire and communicate the physiological signals to data acquisition unit 120, e.g., through a wired or wireless connection. Such sensors may be embodied in various different form factors, such as in the form of a wrist watch, a finger ring, a patch directly attached to a part of user's body, a garment worn by the user, and/or other known form factors for such sensors.

Further, in the context of this disclosure, non-physiological data for user 104 may include location of the user, ambient conditions of the user, internet browsing history of the user, a status of user's stock portfolio, performance of user's preferred sports team or candidate in an election, and/or other information not related with the body or biological features and functions of user 104. As such, data acquisition unit 120 may be communicatively associated with and/or include a location sensor (e.g., a geographical positioning system (GPS)) to determine the location of user 104, one or more sensors to detect temperature, sound level, or level of brightness/darkness of the environment where user 104 is located, a unit that receives and stores user's internet browsing history from one or more user's client devices or from a server accessed by the server and/or other information related to conditions and characteristics of user's activities. Additionally, or alternatively, data acquisition unit 120 may be communicatively associated with and/or include a photo/video camera (facing the user), a microphone and one or more sensors to detect user's gestures. In some embodiments, data acquisition unit 120 includes a memory storage unit and a processor to store and process various received or acquired sensor data, i.e., user information data. For example, using its processing unit, data acquisition unit 120 may be able to process the photo or video information of user 104 to perform facial recognition, and process user's speech detected by the microphone to perform speech recognition. The facial recognition (or facial expression recognition or face detection) may be performed by data acquisition unit 120 based on one or more algorithms including, for example, SHORE™—Sophisticated High-speed Object Recognition Engine (from Fraunhofer Institute for Integrated Circuits) that does recognition of the presence of faces, as well as the recognition of facial expressions ("happy", "surprised", "angry," and "sad"). In general, the facial recognition techniques are based on geometric techniques which include reviewing and analyzing distinguishing features and measure between landmarks, and photometric techniques which provide a statistical approach that summarizes images into values to be compared against templates. Further, the speech recognition by data acquisition unit 120 may be based on one or more speech recognition algorithms including Sphinx algorithms developed at Carnegie-Mellon University, and algorithms based on Hidden Markov models.

In some embodiments, data acquisition unit 120 includes one or more additional components or modules to process and transform the initial sensor data/signals obtained at data acquisition unit 120 into user information data (including user's physiological and non-physiological data) that is used by emotion determination unit 125. For example, data acquisition unit 120 may include modules (not shown) that are capable of amplifying, filtering, multiplexing, digitizing, reducing or eliminating noise, converting digital signals into RF signals, and/or other processing specific to the type of physiological/non-physiological signal to generate the user information data for emotion determination unit 125.

Emotion determination unit 125 receives the user information data from data acquisition unit 120 and processes the data to determine an emotional state of the user. In some embodiments, emotion determination unit 125 processes the user information based on a predetermined computation preference, which may be provided to subsystem 102 by user 104 or the associated organization/group. The predetermined computation preferences may include one or more specific geographical locations, one or more specific events, and one or more specific time periods, which, in general, indicate a trigger for emotion determination unit 125 to begin processing user information and determine an emotional state.

In some embodiments, emotion determination unit 125 uses a supervised (or predictive) machine learning algorithm to determine an emotional state of user 104. Accordingly, as part of supervised learning algorithm, unit 125 relies on a "training set or sample" of user information including a set of specific values of physiological and non-physiological data for which the target property (i.e., an emotional state), for example a classification, is known with confidence. In other words, each known or classified emotional state may be associated with user information including a set of specific values of physiological and non-physiological data which is used as standard user information for that particular emotional state. In some embodiments, the standard user information for a classified emotional state is obtained by exposing a user or a group of users (like users 104) to one or more controlled environments, e.g., including preselected activities or interactions with preselected ambient conditions, and monitoring user's physiological responses and non-physiological conditions for such controlled environments. In general, the monitored user information, i.e., the training set, is representative, i.e., the parameter space covered by the input attributes (related to physiological and non-physiological data) spans that for which the supervised machine learning algorithm is used by emotion determination unit 125. Accordingly, the supervised learning technique is trained on this set of predetermined user information, and the resulting mapping is applied to further user information (e.g., obtained data acquisition unit 120) for which the target emotional state is not available. The additional user information constitutes the "testing set."

Before emotion determination unit 125 uses the machine learning algorithm on data received from data acquisition unit 120, emotion determination unit 125 may preprocess the received data to make it meaningful, and then transform the data in some way as appropriate to the machine learning algorithm. For example, a machine learning algorithm may require "attributes" of the received user information, i.e., the values in the data fields describing the properties of each physiological parameter and non-physiological parameter in the user information, to be numerical or categorical. It is possible to transform numerical data to categorical and vice versa. A common categorical-to-numerical method is scalarization, in which different possible categorical attributes are given different numerical labels, for example, "fast heart rate," "high skin temperature," and "fast speed" may be labeled as the vectors [1, 0, 0], [0, 1, 0], and [0, 0, 1], respectively. Further, numerical data can be made categorical by transformations such as binning. The bins may be user-specified, or can be generated optimally from the data. Binning can create numerical issues, including comparing two floating point numbers that should be identical, objects on a bin edge, empty bins, values that cannot be binned such as NaN, or values not within the bin range.

In general, the user information from data acquisition unit 120 may include a large number of attributes for each physiological parameter and non-physiological parameter, and not all may be required for determining a user emotional state problem. Indeed, use of all attributes may, in some cases, worsen performance. The large number of attributes results in a high-dimensional space with many low density environments or even empty voids. This makes it difficult to generalize from the data and produce useful new results. Therefore, some form of dimension reduction may be employed (by emotion determination unit 125), in which as much of the information as possible is retained, but in fewer attributes. One example of well-known technique to reduce the dimension of the data is principal component analysis (PCA). PCA is limited to linear relations, and produces, as the principal components, the eigenvectors of the input data, i.e., it picks out the directions or attributes which contain the greatest amount of information. The details of the PCA technique are described in "*Principal Component Analysis*," I. T. Jolliffe, Springer Series in Statistics, $2^{nd}$ Edition. Another dimension reduction approach is forward selection, in which one attribute is selected, and selectively new attributes are considered to gain the most information. Or, backward elimination approach may be used, in which all of the attributes are initially selected, and are selectively removed to reduce the number of attributes but maintaining maximum information.

After obtaining appropriate attributes of physiological and non-physiological parameters of the user information and based on the training set, emotion determination unit 125 may use a supervised machine learning algorithm, e.g., support vector machine (SVM) technique to determine an emotional state of user 104. In general, SVM aims to find the hyperplane that best separates two or more classes of data. The input data, i.e., the user information data, are viewed as sets of vectors and the data points closest to the classification boundary are the support vectors. In general, the input user data is arranged in a multidimensional space, for example, in a vector of numerical values comprised of numerical representations of different measured parameters, e.g., for "measured speech stress state," "facial feature state," "measured heart rate," "measured blood pressure," etc. The SVM algorithm creates the decision boundaries in the multi-dimensional space (using a hyper-plane), which are defined in terms of the support vectors, and different divided spaces correspond to different emotional states, e.g., "sad," "happy," "anxious," etc. The input attributes are mapped into a higher-dimensional space using a kernel so that nonlinear relationships within the data become linear, and the decision boundaries, which are linear, are determined in this space. The SVM algorithm minimizes a cost function, which in this case is the number of incorrect classifications. The algorithm has two adjustable hyper-parameters: the width of the kernel, and the regularization, or cost, of classification error, which helps to prevent overfitting of the training set. The shape of the kernel is also an adjustable parameter, a common choice being the Gaussian radial basis function. SVM is generally designed to classify objects into two classes. However, various refinements may be made to the SVM algorithm to support additional classes, and to perform regression, i.e., to supply a continuous output value instead of a classification. Classification probabilities can be output, for example, by using the distance of a data point from the decision boundary. The details of the SVM algorithm can be found in "*The Nature of Statistical Learning Theory*," V. Vapnik, 2nd Edition (Springer, N.Y., 1999), "*An Introduction to Support Vector Machines and Other Kernel-based Learning Methods*," N. Cristianini and J. Shawe-Taylor, (Cambridge University Press, 2000), and "*Learning and Soft Computing: Support Vector Machines, Neural Networks, and Fuzzy Logic Models*," V. Kecman (MIT Press, Cambridge, Mass., 2001).

For example, user information from data acquisition unit 120 may include data indicating that user 104 is smiling (based on facial recognition), has a steady voice tone (based on speech analysis and recognition), is performing open gestures (based on gesture recognition), is currently located at a shopping mall (based on GPS-determined coordinates) or accessing an online retailer (based on the browsing history). This information may be provided to emotion determination unit 125 to be processed according to the SVM technique and estimate that user 104 is in a "happy" emotional state. Similarly, user information from data acquisition unit 120 may include data indicating that user 104 is frowning, speaking at an elevated voice level, is performing abrupt or sudden gestures, is currently located at a bar. This information may be provided to emotion determination unit 125 to be processed according to the SVM technique and estimate that user 104 is in an "unhappy" emotional state.

In some embodiments, emotion determination unit 125 is configured to use other supervised machine learning algorithms, such as, but not limited to, artificial neural network technique, decision tree algorithm, and k nearest neighbor method. Further, emotion determination unit 125 is configured to use unsupervised methods such as, but not limited to, kernel density estimation method, K-means clustering method, and expectation maximization method. Another machine learning algorithm that may be used is a fuzzy classifier which permits finer gradations of user emotional state, such as "happy" or "sad" on a particular scale, e.g., scale of value 1 to value 10.

Emotion determination unit 125 may convey the determined or estimated emotional state of user 104 to emotion reporting unit 130. In some embodiments, emotion reporting unit 130 communicates the emotional state, e.g., based on a predetermined reporting preference, to application(s) functional on user device(s) 110 associated with or operated by user 104, such that an entity is notified of the user's emotional state. In some embodiments, the predetermined reporting preference is preselected by the user, and stored in a memory accessible by the emotion reporting unit. The predetermined reporting preferences may include one or more specific geographical locations, one or more specific events, and one or more specific time periods, which, in general, indicate a trigger for emotion reporting unit 130 to begin communicating the emotional state to the application. User device(s) 110 to which the emotional state is communicated may be a computing and/or a communication device capable of connecting to one or more networks, such as, the Internet, a cellular network, a wired network, etc. The user device(s) may include a mobile phone, a smartphone, a tablet computer, a personal computer, a laptop, a smartphone, a gaming device, or a wearable device in the form of a wrist watch, a bracelet, a pair of headphones, a pair of eyeglasses and/or other wearable computing devices.

In some embodiments, the application functional on the user device(s) may be a social-networking application (e.g., Facebook, Twitter, LinkedIn, Google+, etc.) which the user is authorized to access as a member thereof. Accordingly, as part of communicating the emotional state of the user, emotion reporting unit 130 may store software code which when executed (by a processor of unit 130 or subsystem 102, or any other processor) be configured to automatically activate the application (e.g., a social networking application) on the user device, provide user identification information to be authenticated by the application for logging the user into the application, and provide a message including an indication of the determined emotional state of the user to be shared with other members (e.g., "friends," "followers," "connections," etc.) of the application. For example, the emotional state of user 104 may be shared as a message with other members of the social network on a platform provided by that application, e.g., as a "what's on your mind?" message update on Facebook, a "tweet" on Twitter, etc. In some other embodiments, instead of, or in addition to, the social networking application(s), the application includes a short message service (SMS) application, an e-mail application, etc. As such, emotion reporting unit 130 may be configured to communicate the emotional state of user 104 by automatically generating and transmitting a SMS message or an e-mail message, e.g., to a predetermined set of recipients listed in an address book at the user device(s) 110. Emotion reporting unit 130 may be further configured to request a confirmation from user 104 to communicate or share the emotional state (using the application), and receive the confirmation from user 104 before communicating or sharing the emotional state.

In some embodiments, emotion history unit 135 is configured to track and store emotional states of the user determined by emotion determination unit 125, e.g., based on one or more tracking criteria, e.g., user's past locations, for a past time period, browsing history, etc. Emotion history unit 135 may then process the emotional states to determine an effect on the user caused due to the emotional states relative to the tracking criterion. For example, emotion history unit 135, based on the tracked information, may present automated analytic information to inform user 104 whether certain combinations of context (location, time, etc.) and other factors have a negative or positive influence on the emotional state or mood of user 104. Emotion history unit 135 may also be able provide preventive strategies, or automatically alter the user's itinerary to improve mood (e.g., change the default driving navigation plan or reschedule a typically stressful meeting to a better time of day for the user). In addition, emotion history unit 135 may be configured to relay or report user's emotional state history user's health professional.

As discussed above, users 104 may be members of a same organization, e.g., a company, an educational institution, a social network, a city, a state, a country, etc. Alternatively, users 104 may be considered as a single group by virtue of being present in a same geographical area (e.g., a shopping mall) or at a same event (e.g., a concert) at the same time. In some embodiments, each subsystem 102 of each user 104 in the organization or group communicates data or information including the determined emotional state of the respective user 104 through the respective emotion reporting unit 130 to group emotion determination unit 140. The emotional state data of users 104 may be provided to unit 140 directly and/or via one or more (wired or wireless) networks 118. In some embodiments, group emotion determination unit 140 is configured to process the received emotional states of users to determine an emotional state of the organization, e.g., using one or more similar machine learning techniques used by emotion determination unit 125 (discussed above). Additionally, in some embodiments, before determining the emotional state of the organization, group emotion determination unit 140 removes or deletes information identifying users 104 from the received data which includes the emotional state of the respective users such that user privacy and security is maintained. In some embodiments, after determining the emotional state of a group of people (e.g., that present in a certain section of a mall), group emotion determination unit 140 (or an associated unit) is configured to provide marketing options (e.g., discount options for one or more stores in the mall) to that group of people based on the collective emotional state (e.g., "happy" state), e.g., based on the mall's public announcement system or other systems.

In some embodiments, subsystem 102 (or units thereof) is embodied in an electronic, computing and communication device of one of various form factors. Such device may be a mobile phone, a tablet computer, a personal computer, a server, a laptop, a smartphone, a gaming device, a networking device, or a wearable computing device in the form of a wrist watch, a bracelet, a pair of headphones, a pair of eyeglasses and/or other wearable computing devices. In some embodiments, subsystem 102 (or units thereof) is completely or partially implemented by one or more processing units implanted within user 104. Subsystem 102 (or units thereof) may be part of device 110.

In some embodiments, device implementing subsystem 102 includes a display device, input devices, a memory, a system-on-chip (SoC) chipset, a communication module, and an antenna. The device may also include a bus and/or other interconnection means to connect and communicate information between various components or units of the device.

The display device may be configured to display information to a user and may comprise a liquid crystal display (LCD), a light emitting diode (LED)-based display, or any other flat panel display, or may use a cathode ray tube (CRT). The input devices may include alphanumeric and other keys which may be inputted via a keyboard, touch screen (e.g., with haptics or tactile feedback), speech input, eye tracking input, brain monitoring systems or other comparable input mechanism. The input information received through one or more of the input devices may be communicated to a processor of the SoC, e.g., via a bus, for further processing. Another type of the input device may include a cursor control device, such as a mouse, a trackball, or cursor direction keys to communicate direction information and command selections, e.g., to the SoC and to control cursor movement on the display device.

The memory of the subsystem device (or any other part of system 100) may be a dynamic storage device configured to store information and instructions to be executed by processors of the SoC and/or other processors (or computing units). The memory may also be used to store temporary variables or other intermediate information during execution of instructions by the processors. Some or all of the memory may be implemented as Dual In-line Memory Modules (DIMMs), and may be one or more of the following types of memory: Static random access memory (SRAM), Burst SRAM or SynchBurst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), or any other type of memory device. The device may also include read only memory (ROM) and/or other static storage device configured to store static information and instructions for processors of the SoC and/or other processors (or computing units). Further, the device may include a magnetic disk, optical disc or flash memory devices to store information and instructions.

In some embodiments, the SoC is part of a core processing or computing unit of the subsystem device, and is configured to receive and process input data and instructions, provide output and/or control other components of subsystem 102 in accordance with embodiments of the present disclosure. The SoC may include a microprocessor, a memory controller, a memory and peripheral components. The microprocessor may further include a cache memory (e.g., SRAM), which along with the memory of the SoC may be part of a memory hierarchy to store instructions and data. The microprocessor may also include one or more logic modules such as a field programmable gate array (FPGA) or other logic array. Communication between the SoC's microprocessor and memory may be facilitated by the memory controller (or chipset), which may also facilitate in communicating with the peripheral components, such as counter-timers, real-time timers and power-on reset generators. The SoC may also include other components including, but not limited to, timing sources (e.g., oscillators and phase-locked loops), voltage regulators, and power management circuits.

In some embodiments, the device implementing is configured to communicate with other devices or systems directly or via one or more networks using a communication module. The communication module may include necessary and typical hardware, software and/or firmware modules, e.g., related to a modulator, a demodulator, a baseband converter, a channel codec, and/or other components, implemented therein to enable the device for wireless communication. As such, the communication module is able to wirelessly transmit and receive data and messages in form of radio frequency (RF) signals through an antenna. In some embodiments, the communication module is designed and configured to support communication based on one or more communication standards and protocols including, but not limited to, Wi-Fi, Wi-Gi, Bluetooth, GSM, CDMA, GPRS, 3G or 4G (e.g., WiMAX, LTE) cellular standards, Wireless USB, satellite communication, and Wireless LAN. Additionally, or alternatively, the communication module may also be configured for wired communication, e.g., based on the Ethernet standard, and as such, may be coupled to an appropriate network interface of the device.

Figure 2:
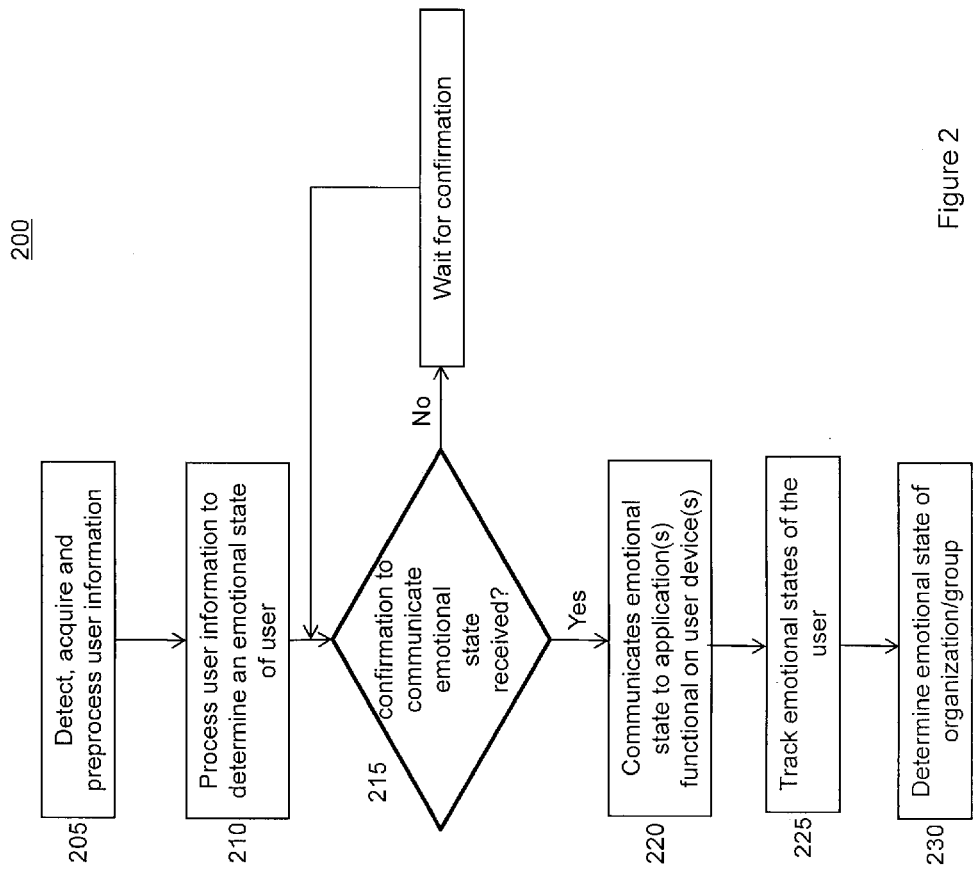
FIG. 2 is a flowchart of a method to determine an emotional state of a user and a group of users, in accordance with various embodiments of the present disclosure.

Referring now to FIG. 2 which is flowchart of a method 200 to determine an emotional state of a user 104 within system 100, e.g., using subsystem 102, in accordance with various embodiments disclosed herein. For example, method 200 may commence at operation 205 in which data acquisition unit 120 detects, acquires and/or processes user information including physiological and non-physiological data associated with user 104. As discussed above, data acquisition unit 120 detects and obtains user's physiological and non-physiological data via one or more sensors and other devices (e.g., a camera, a microphone, etc.) that are associated with user 104 and/or part of data acquisition unit 120. Data acquisition unit 120 may process and transform the obtained sensor data/signals into user information data (including user's physiological and non-physiological data) that is used by emotion determination unit 125 further in method 200. For example, data acquisition unit 120 may amplify, filter, multiplex, digitize, reduce or eliminate noise, convert digital signals into RF signals, and/or perform other processing specific to the type of physiological/non-physiological signal to generate the user information data.

Further, in operation 210, the user information is processed, e.g., by emotion determination unit 125 to determine an emotional state of user 104. Emotion determination unit 125 may preprocess and transform the user information, and use one or more machine learning techniques (e.g., SVM technique) to process the transformed data to determine the emotional state, as discussed above.

In operation 215, emotion reporting unit 130 receives the emotional state of user 104 from emotion determination unit 125, and requests a confirmation from user 104 to communicate or share the emotional state. If emotion reporting unit 130 receives the confirmation, in operation 220, emotion reporting unit 130 communicates data including the emotional state to an application(s) functional on user device(s) 110 associated with or operated by user 104 and to group emotion determination unit 140. In some embodiments, emotion reporting unit 130 conveys the emotional state according to the predetermined reporting preference which may be preselected by the user and stored in a memory accessible by the emotion reporting unit.

As discussed above, the application functional on the user device(s) 110 may be a social-networking application (e.g., Facebook, Twitter, LinkedIn, Google+, etc.) which the user is authorized to access as a member thereof. Accordingly, as part of communicating the emotional state of the user, emotion reporting unit 130 may, among other operations, provide a message including an indication of the determined emotional state of the user to be shared with other members (e.g., "friends," "followers," "connections," etc.) of the application, or provide a SMS message or an e-mail message, e.g., to a predetermined set of recipients listed in an address book at the user device(s) 110.

Further, in operation 225, emotional states of the user are tracked by emotion history unit 135, e.g., based on one or more tracking criteria, e.g., user's past locations, for a past time period, browsing history, etc. Emotion history unit 135 may then process the emotional states to determine an effect on the user caused due to the emotional states relative to the tracking criterion. Emotion history unit 135 may also be able to provide preventive strategies, or automatically alter the user's itinerary to improve mood (e.g., change the default driving navigation plan or reschedule a typically stressful meeting to a better time of day for the user).

In operation 230, each subsystem 102 of each user 104 in the organization or group communicates data or information including the determined emotional state of the respective user 104 through the respective emotion reporting unit 130 to group emotion determination unit 140 (e.g., via one or more networks 118): Group emotion determination unit 140 processes the received emotional states of users to determine an emotional state of the organization/group, e.g., using one or more similar machine learning techniques used by emotion determination unit 125 (discussed above). Additionally, in some embodiments, before determining the emotional state of the organization, group emotion determination unit 140 removes or deletes information identifying users 104 from the received data which includes the emotional state of the respective users.

Various embodiments herein are described as including a particular feature, structure, or characteristic, but every aspect or embodiment may not necessarily include the particular feature, structure, or characteristic. Further, when a particular feature, structure, or characteristic is described in connection with an embodiment, it will be understood that such feature, structure, or characteristic may be included in connection with other embodiments, whether or not explicitly described. Thus, various changes and modifications may be made to this disclosure without departing from the scope or spirit of the inventive concept described herein. As such, the specification and drawings should be regarded as examples only, and the scope of the inventive concept to be determined solely by the appended claims.

What is claimed is:

1. A system to determine an emotional state of a user, the system comprising:
    a data acquisition unit configured to detect user information, the user information including physiological and non-physiological data associated with the user;
    an emotion determination unit operatively connected to the data acquisition unit and configured to process the user information to reduce a number of attributes of the user information and determine an emotional state of the user based on the user information with the reduced number of attributes; and an emotion reporting unit configured to communicate the emotional state based on a predetermined reporting preference to an application of a communication device, wherein the application is configured to share the emotional state of the user such that an entity is notified of the user's emotional state.

2. The system of claim 1, wherein the data acquisition unit comprises at least one of a camera, a microphone, an accelerometer, a gyroscope, a location sensor, a temperature sensor to detect ambient temperature, a gesture recognition sensor, and a sensor to detect a physiological parameter of the user.

3. The system of claim 1, wherein the non-physiological data comprises location of the user, ambient temperature of the user, and internet browsing history of the user.

4. The system of claim 1, wherein the emotion determination unit processes the user information based on a predetermined computation preference.

5. The system of claim 1, wherein the predetermined reporting preference comprises a specific user location or a specific time period.

6. The system of claim 4, wherein the predetermined computation preference comprises a specific user location or a specific time period.

7. The system of claim 1, wherein the emotion reporting unit is further configured to request a confirmation from the user to communicate the emotional state, and receive the confirmation before communicating the emotional state.

8. The system of claim 1, wherein at least one of the data acquisition unit, the emotion determination unit, and the emotion reporting unit is embodied in a mobile phone, a tablet computer or a wearable computing device, or implanted within the user.

9. The system of claim 8, wherein the wearable computing device is a wrist watch, a bracelet, a pair of headphones, or a pair of eyeglasses.

10. The system of claim 1, wherein the application is a social-networking application which the user is authorized to access.

11. The system of claim 1, further comprising an emotion history unit configured to track and store emotional states of the user determined by the emotion determination unit based on a predetermined tracking criterion, and process the emotional states to determine an effect on the user caused due to the emotional states relative to the tracking criterion.

12. The system of claim 1, wherein the user is a member of an organization including a plurality of users other than the user, the system further comprising a group emotion determination unit configured to receive the emotional state of the user and an emotional state of another of the plurality of the users, and process the emotional states to determine an emotional state of the organization.

13. A method to determine an emotional state of a user, the method comprising:
  detecting user information, the user information including physiological and non-physiological data associated with the user;
  processing the user information to reduce a number of attributes of the user information and determine an emotional state of the user based on the user information with the reduced number of attributes; and
  communicating the emotional state based on a predetermined reporting preference to an application of a communication device associated with the user, wherein the application is configured to share the emotional state of the user such that an entity is notified of the user's emotional state.

14. The method of claim 13, wherein said detecting comprises detecting the user information using at least one of a camera, a microphone, an accelerometer, a gyroscope, a location sensor, a temperature sensor to detect ambient temperature, a gesture recognition sensor, and a sensor to detect a physiological parameter of the user.

15. The method of claim 13, wherein the non-physiological data comprises location of the user, ambient temperature of the user, and internet browsing history of the user.

16. The method of claim 13, wherein the predetermined reporting preference comprises a specific user location or a specific time period.

17. The method of claim 13, further comprising requesting a confirmation from the user to communicate the emotional state; and receiving the confirmation before communicating the emotional state.

18. The method of claim 13, wherein the application is a social-networking application which the user is authorized to access.

19. The method of claim 13, further comprising tracking emotional states of the user based on a predetermined tracking criterion; and processing the emotional states to determine an effect on the user caused due to the emotional states relative to the tracking criterion.

20. The method of claim 13, wherein the user is a member of an organization including a plurality of users other than the user, the method further comprising receiving the emotional state of the user and an emotional state of another of the plurality of the users; and processing the emotional states to determine an emotional state of the organization.

21. A non-transitory computer-readable medium comprising computer readable code physically embodied thereon which, when executed by a processor causes the processor to carry out functions comprising:
  detecting user information, the user information including physiological and non-physiological data associated with the user;
  processing the user information to reduce a number of attributes of the user information and determine an emotional state of the user based on the user information with the reduced number of attributes; and
  communicating the emotional state based on a predetermined reporting preference to an application of a communication device associated with the user, wherein the application is configured to share the emotional state of the user such that an entity is notified of the user's emotional state.

22. The computer-readable medium of claim 21, wherein said detecting comprises detecting the user information using at least one of a camera, a microphone, an accelerometer, a gyroscope, a location sensor, a temperature sensor to detect ambient temperature, a gesture recognition sensor, and a sensor to detect a physiological parameter of the user.

23. The computer-readable medium of claim 21, wherein the non-physiological data comprises location of the user, ambient temperature of the user, and internet browsing history of the user.

24. The computer-readable medium of claim 21, wherein the predetermined reporting preference comprises a specific user location or a specific time period.

25. The computer-readable medium of claim 21, wherein the functions further comprise requesting a confirmation from the user to communicate the emotional state; and receiving the confirmation before communicating the emotional state.

26. The computer-readable medium of claim 21, wherein the application is a social-networking application which the user is authorized to access.

27. The computer-readable medium of claim 21, wherein the functions further comprise tracking emotional states of the user based on a predetermined tracking criterion; and processing the emotional states to determine an effect on the user caused due to the emotional states relative to the tracking criterion.

28. The computer-readable medium of claim 21, wherein the user is a member of an organization including a plurality of users other than the user, the functions further comprising receiving the emotional state of the user and an emotional state of another of the plurality of the users; and processing the emotional states to determine an emotional state of the organization.

29. The computer-readable medium of claim 21, wherein the processor is embodied in a mobile phone, a tablet computer or a wearable computing device, or implanted within the user.

30. The computer-readable medium of claim 29, wherein the wearable computing device is a wrist watch, a bracelet, a pair of headphones, or a pair of eyeglasses.

* * * * *